(12) United States Patent
Gergely et al.

(10) Patent No.: US 6,190,697 B1
(45) Date of Patent: Feb. 20, 2001

(54) EFFERVESCENT FORMULATION CONTAINING PLANT EXTRACT

(75) Inventors: Gerhard Gergely, Gartengasse 8, A-1053 Vienna; Irmgard Gergely, Vienna; Thomas Gergely, Vienna; Stefan Gergely, Vienna, all of (AT)

(73) Assignee: Gerhard Gergely (AT)

( * ) Notice: Under 35 U.S.C. 154(b), the term of this patent shall be extended for 0 days.

(21) Appl. No.: 09/178,639

(22) Filed: Oct. 26, 1998

(30) Foreign Application Priority Data

Oct. 27, 1997 (EP) .................................................. 97118648

(51) Int. Cl.$^7$ ........................................................ A61K 9/46
(52) U.S. Cl. ........................ 424/466; 424/469; 424/476; 424/195.1
(58) Field of Search .............................. 424/466, 195.1, 424/469, 476

(56) References Cited

U.S. PATENT DOCUMENTS

| | | | | |
|---|---|---|---|---|
| 4,127,645 | * | 11/1978 | Witzel et al. ........................... | 424/44 |
| 5,171,571 | * | 12/1992 | Stephan et al. .................... | 424/195.1 |
| 5,219,574 | * | 6/1993 | Wehling et al. ...................... | 424/464 |
| 5,262,162 | * | 11/1993 | Bormann et al. .................. | 424/195.1 |
| 5,415,870 | * | 5/1995 | Gergely et al. ....................... | 424/466 |
| 5,633,004 | * | 5/1997 | Nihimura et al. .................... | 424/438 |

FOREIGN PATENT DOCUMENTS

| | | |
|---|---|---|
| 9003179 | 4/1990 | (WO) . |
| 9729642 | 8/1997 | (WO) . |

* cited by examiner

*Primary Examiner*—Thurman K. Page
*Assistant Examiner*—Isis Ghali
(74) *Attorney, Agent, or Firm*—Rothwell, Figg, Ernst & Manbeck

(57) ABSTRACT

The effervescent formulation elation in the form of granules or of a tablet contains, in addition to the effervescent base, at least one water-soluble or at least suspendable plant extract whose particles are coated with at least one oily, fatty or waxy substance. At least one emulsifier and/or at least one antifoam may be present in the coating and/or as a further component of the mixture, in particular applied as a further component of the mixture to a pharmaceutically permissible filler as carrier. The individual phases are prepared by a procedure in which the plant extract or the filler is heated—preferably in a granulator, in particular in a vacuum granulator—and wet or mixed with a melt or solution of the oily, fatty or waxy substance or at least one emulsifier and/or at least one antifoam and then dried—preferably in a vacuum—and sieved to the desired particle size.

23 Claims, No Drawings

EFFERVESCENT FORMULATION CONTAINING PLANT EXTRACT

The invention relates to an effervescent formulation according to the preamble of claim 1. Plant extracts have long been a popular dosage form for prophylaxis and therapy; they are becoming more important, not least owing to the increasing elucidation of the action mechanism and of the structure of the active ingredients. Where higher doses are necessary, instant tea has to date been the most important dosage form but has some disadvantages, namely on the one hand the inexact dosage as a result of dissolving a teaspoon or tablespoon of the instant tea in water, It being scarcely possible exactly to maintain the fill-weight; on the other hand, the instant teas containing plant extracts and usually present in powder or granular form are very hygroscopic and agglomerate in a container after the latter has been opened a few times.

In order to avoid these disadvantages and to provide an attractive dosage form, the administration of the plant extracts in the form of an effervescent tablet was developed. However, it has been found that in particular the very water-soluble plant extracts, which are generally present in a finely pulverulent form spray-dried from aqueous and/or alcoholic solution, slow down the dissolution of the effervescent tablet to an extreme extent. These include, inter alia, ivy and sabale dry extracts, solidago, plantago, nettle root, nettle leaf, birch leaf, cynara and thyme extracts, extracts of hypericum, harpagophytum, gingko and ruscus (Extractum Rusci aculeati). The dissolution is slowed down because, on admission of water, these very soluble plant extracts very rapidly form highly concentrated, tacky, slimy solutions which prevent the further admission of water to the interior of the tablet, thus hindering rapid dissolution. Moreover, effervescent particles which are intended to promote disintegration and dissolution of the tablet are also coated with the solution and their reaction with the water is thus suppressed. In addition, most plant extracts contain saponin and consequently exhibit extreme foaming behavior in the effervescent tablet. The dissolution is thus further slowed down because frothy, highly concentrated solutions form between the effervescent particles.

Thus, for example when a dose of 400 mg of solidago extract is added to effervescent granules which are then compressed to form tablets, dissolution times of 15 to 20 minutes result on dissolution in water. Even smaller amounts, for example 65 mg of an ivy dry extract in an effervescent tablet, exhibit dissolution times of 5 to 7 minutes or more on dissolution in water at 17° C. This no longer meets the requirements of pharmacopoeias, according to which the dissolution time of effervescent tablets in water at 20° C. should be less than 5 minutes.

By means of conventional measures, such as, for example, by the addition of antifoams, such as, for example, simethicone or dimethicone, or by the application of the antifoam to the dry plant extract itself it was possible to achieve only a slight improvement by reducing the foaming and—associated with this—also only a slight reduction in the dissolution time of the effervescent tablet.

Granulation of the plant extracts with the object of increasing the size of the particles and reducing their number within the effervescent tablet in order thus to prevent the formation of a concentrated solution around the plant extract particles and effervescent particles during dissolution of the tablet in water also did not achieve the object since precisely these granulated particles then agglomerated to an extreme extent and exhibited undesired and by no means rapid dissolution properties.

Binding to a slightly soluble substance also did not lead to a short dissolution time since the extracts at the surface of the slightly soluble substance likewise formed highly concentrated solutions and thus rendered this measure ineffective.

Although granulation with slightly soluble substances once again resulted in the effervescent tablet with plant extracts dissolving somewhat more rapidly, the granulated particles could not dissolve completely and formed a residue.

The object of the invention was therefore to provide a galenical formulation for freely soluble plant extracts in the form of an effervescent tablet, which formulation has a dissolution time of less than 4 minutes and significantly reduced foam formation.

Surprisingly, the achievement of this object and the overcoming of the above-mentioned problems were possible for the first time by the measures described in the defining clause of claim 1. Particular embodiments and further developments of the concept of the invention are described in the defining clauses of the dependent claims.

The invention comprises treating the plant extract with at least one fatty, oily or waxy substance, in particular producing a thin coating film of this substance or these substances on the plant extract particles, preferably emulsifiers also being added to this hydrophobic extract phase with fatty, oily or waxy substances. The fatty, oily or waxy substances can be applied to the plant extract particles either in the molten state or in solution in a solvent in which the emulsifiers too are soluble. The plant extracts treated in this manner can then—optionally with further addition of the emulsifier—be mixed with effervescent granules and the mixture compressed to give tablets. Effervescent tablets containing plant extracts which dissolve in water at 17° C. within 1½ to 4 minutes are obtained.

As a result of the treatment with the above-mentioned substances, the plant extracts become sufficiently hydrophobic to prevent conversion of the effervescent tablet into a paste on dissolution of water, so that the effectiveness of the effervescent particles on admission of water is displayed as desired and rapid dissolution of the tablet is thus permitted. As a result of the contact with water, the effervescent particles display their effervescent activity and the plant extract particles are ejected from the tablet owing to the hydrophobic structure and because of the effervescent effect and dissolve only thereafter. It has proven advantageous to add suitable emulsifiers to the phase containing the fatty, oily or waxy substances, in order to achieve appropriate suspension properties for these substances on dissolution of the effervescent tablet in water.

In particular, the following substances can be used as fatty, oily or waxy substances which are suitable for the surface treatment of the plant extract particles: esters of medium-chain, vegetable fatty acids, such as, for example, caprylic and capric acid, with glycerol and propylene glycol, preferably Miglyol® neutral oils.

Furthermore, all edible, animal and vegetable fats may be used as fat components. These are in particular triglycerides which essentially consist of mixtures of glyceryl esters of higher fatty acids, in particular of vegetable or animal origin, having a chain length of about 10 to 22 C atoms. These include, for example, microcrystalline triglycerides and glyceryl esters of saturated, linear and unbranched fatty acids, e.g. glyceryl trimyristate, glyceryl tripalmitate, trimyristin, etc. Further suitable fat components are, for example, coconut oil, hydrogenated coconut oil, hydrogenated castor oils, tocopheryl acetate, esters of higher fatty acids, such as, for example, isopropyl palmitate, polyethylene glycol, such as, for example, Carbowax®, it being possible to use Carbowax® 400 or Carbowax® 6000, depending on the plant extract.

The fat, oily or waxy substances are used in an amount of 0.5 to 25 parts by weight, preferably 0.8–19 parts by weight, based on 100 parts by weight of the freely soluble plant extract, these substances being at least partly contained in the plant extract phase but possibly also additionally being added as a separate fat phase to the effervescent granules. The emulsifiers are on the one hand applied together with the fatty, oily or waxy substances directly to the plant extract and optionally on the other hand added in the form of a phase, the emulsifier being applied with suitable solvents to a carrier, the solvent being evaporated off and this emulsifier phase being mixed with the effervescent tablet.

A variety of emulsifiers may be used, depending on the fatty, oily or waxy substances employed. Phospholipids, such as lecithin, Metarin and Epikuron, furthermore polysorbates (sorbitan monolaurate, etc.) and ethoxylated glycerol fatty acid esters (e.g. Tagat®), sugar esters, glycerol polyethylene glycol oxystearate (Cremophor RH 40), Macrogol glycerol ricinoleate or sodium stearoyllactate are recommended. It is also possible to use wetting agents, such as sodium dioctylsulfosuccinate or sodium laurylsulphate. One or more emulsifiers can be incorporated into the plant extract phase and/or also added in a further emulsifier phase to the final mixture for the ready-to-press granules. The amount of emulsifier is between 0.2 and 10, preferably 0.3–8, parts by weight, based on 100 parts by weight of the freely soluble plant extract to be used, some emulsifiers, owing to their oily property, also enhancing the effectiveness of the fatty substances and some lipids also having an emulsifier character, such as propylene glycol stearate and glyceryl oleate, laurate and stearate.

In order, if required, to impart better flowability to the extracts treated with fatty, oily or waxy substances, it is possible to add a fine filler which adheres to the fatty surface and thus prevents the agglomeration of the active ingredient phase. All conventional pharmaceutical tablet fillers suitable for this purpose, such as sugar alcohols, mannitol, sorbitol and furthermore maltodextrin, pulverized sucrose, pulverized lactose, fructose, glucose, etc. These fillers can be introduced directly into the plant extract phase (cf. Example 1), or the plant extract phase is homogeneously mixed with a filler after the preparation and then mixed with the effervescent granules containing the remaining ingredients, flavors, etc.

For example, mannitol or sorbitol takes up a part of the oily, fatty or waxy substance and also the emulsifier and prevents the agglomeration of the coated particles of the plant extract phase. Incidentally, the fillers mentioned are also suitable as carriers for the emulsifier or emulsifiers, for the antifoam or antifoams and for any additional amounts of oily, fatty or waxy substance, particularly when the absorptivity of the plant extract particles for these substances on the surface is not sufficient for achieving the optimum effect.

The preparation of the plant extract phase can be carried out as follows: the freely soluble plant extracts are preheated to 45 to 60° C.; a solution or melt of the fatty, oily or waxy substances—preferably with one or more emulsifiers—is applied. This solution is uniformly distributed while stirring, and the solvent is then evaporated, preferably by means of a vacuum Before drying, it is also possible to add a filler.

To reduce foam formation, it is necessary in most cases, but not essential, to add an antifoam, which on the one hand can be introduced into the fat/emulsifier phase but on the other hand may also be added as a separate phase to a mixture of the effervescent granules and the plant extract phase, the antifoam being applied to a neutral excipient or filler. For the preparation of the antifoam phase, the antifoam is applied to a filler by means of a solvent or of an aqueous suspension; the solvent is evaporated off, and this phase is added to the tablet.

The amount of antifoam used, based on 100 parts by weight of plant extract, may be between 0 and 10 parts by weight, i.e. in the case of freely soluble plant extracts having a low saponin content the use of an antifoam is not required in specific cases.

However, it is also possible to add the oily, fatty or waxy substance and any intended emulsifiers and/or antifoams to the solution intended for the preparation of the plant extract for spray-drying.

All conventional effervescent components may be used for the preparation of the effervescent base or of the effervescent granules, the acid component preferably consisting of citric acid, tartaric acid, malic acid or of the salts thereof, such as, for example, monosodium citrate or monosodium tartrate. The base fraction of the effervescent base expediently consists of $CO_2$-eliminating alkali metal bicarbonates or carbonates, such as sodium and/or potassium bicarbonate or carbonate, and partly, but not exclusively, of alkaline earth metal carbonates, such as calcium carbonate and/or magnesium carbonate.

In particular, sweeteners, such as sugar, sodium cyclamate, saccharin sodium, aspartame and acesulfame, and flavors or other galenical fillers, such as sugar alcohols, e.g. mannitol and sorbitol, and also maltodextrin, optionally sucrose, fructose, lactose, etc., may be used as additives and excipients.

The effervescent plant extract formulation prepared according to the invention is distinguished by rapid dissolution in water (dissolution time at 17° C., 1½ to 4 minutes) and by substantially improved foaming behavior, i.e. only slight foaming.

The invention is illustrated in more detail below with reference to an example. Further examples of various plant extracts are summarized in a table.

EXAMPLE 1

Effervescent Ivy Extract Tablet

Preparation of the ivy extract phase:

65 parts by weight of ivy dry extract are heated to about 45–50° C. The dry extract is treated with a solution of 5 parts by weight of simethicone, 2 parts by weight of a triglyceride of caprylic and capric acid (Miglyol 812®), 0.2 parts by weight of Tagat® R40 (ethoxylated glycerol fatty acid ester), in 1.7 parts by weight of butanone and 0.7 parts by weight of 96% ethanol. This solution is distributed over the ivy dry extract while stirring, and 100 parts by weight of mannitol are added before drying. The product is then dried by means of a vacuum with slow stirring and the phase is sieved to 0.5 mm.

In this case, both the oily substance and the emulsifier and the antifoam simethicone are applied to the ivy dry extract in one step.

The effervescent granules are prepared using the following ingredients and amounts: 1165 parts by weight of crystalline citric acid, 250 parts by weight of citric acid powder, 3 parts by weight of saccharin sodium and 50 parts by weight of sodium cyclamate were heated to 60° C. and moistened with a solution of 5 parts by weight of sodium citrate and 5.5 parts by weight of water. Thereafter, 897 parts by weight of sodium bicarbonate are added and allowed to react in a controlled manner. Before drying, 88 parts by weight of sodium carbonate are added and the product is then dried by means of a vacuum at a temperature above 50° C. down to 15 mbar.

For the ready-to-press granules, 172.2 parts by weight of the plant extract phase are mixed with 2458 parts by weight of an effervescent base and 200 parts by weight of sorbitol, 298 parts by weight of mannitol and 60 parts by weight of flavor and 210 parts by weight of maltodextrin and compressed to give tablets of 3.4 g. For flavoring, it is also possible to add a fruit powder in an amount of 250 to 270 parts by weight instead of the maltodextrin.

The product exhibits little foam formation and a dissolution time of 2½ to not more than 3 minutes, a comparable effervescent tablet without treated plant extract exhibiting a dissolution time of 5 to 7 minutes.

Examples 2 to 17 with further freely soluble plant extracts are shown in Tables 1 to 4 below, the preparation essentially corresponding to the preparation of Example 1.

TABLE 1

| Example No. | 2 Ivy | 3 Birch leaves | 4 Cynara | 5 Thyme |
|---|---|---|---|---|
| Effervescent base | 73.60 | 63.80 | 84.79 | 73.63 |
| Active ingredient phase | | | | |
| Active ingredient | 1.99 | 11.80 | 14.62 | 8.57 |
| Fatty/oily/waxy substance: | | | | |
| Isopropyl palmitate | | | 0.46 | |
| Macrogol glycerol ricinoleate | | | | 0.57 |
| Triglyceride of caprylic and capric acid (Miglyol ®) | 0.06 | | | |
| Polyethylene glycol (Carbowax) | | 0.78 | | |
| % by wt., based on active ingredient | 3.02 | 6.61 | 3.15 | 6.65 |
| Emulsifiers: Sorbitan monolaurate | | | 0.05 | |
| Polyoxyethylene glycerol fatty acid ester (Tagat ®) | 0.01 | | | |
| Soya lecithin | | 0.10 | | 0.09 |
| + mono- and diglycerides (Metarin ®) | | | | |
| % by wt., based on active ingred. | 0.50 | 0.85 | 0.34 | 1.05 |
| Antifoam: Simethicone | 0.15 | | | |
| % by wt., based on active ingred. | 7.54 | | | |
| Filler: Mannitol | 2.99 | 9.44 | | 5.71 |
| Admixture | | | | |
| Emulsifier Magnesium stearate | | | 0.09 | |
| Mannitol | | 5.1 | | 5.60 |
| Docusate sodium | | 0.10 | | 0.11 |
| Emulsifier: % by wt., based on active ingred. | | 0.85 | 0.62 | 1.28 |
| Antifoam phase Mannitol | | 5.21 | | 5.68 |
| Simethicone | | 0.02 | | 0.03 |
| Antifoam: % by wt., based on active ingred. | | 0.17 | | 0.35 |
| Fillers Mannitol | 8.93 | | | |
| Sorbitol | 5.99 | 3.64 | | |
| Maltodextrin | 6.29 | | | |
| Sum | 100 | 100 | 100 | 100 |
| Total (% by wt., based on active ingred.) | | | | |
| Fatty/oily/waxy substance: | 3.02 | 6.61 | 3.15 | 6.65 |
| Emulsifier: | 0.50 | 1.70 | 0.96 | 2.33 |
| Antifoam: | 7.54 | 0.17 | | 0.35 |
| Tablet weight [mg] | 3340 | 1850 | 3480 | 3500 |
| Dissolution time [sec] | 120 | 140 | 140 | 100 |

TABLE 2

| Example No. | 6 Plantago | 7 Plantago | 8 Fol.Urticae | 9 Rad.Urticae |
|---|---|---|---|---|
| Effervescent base | 76.63 | 68.88 | 61.75 | 86.89 |
| Active ingredient phase | | | | |
| Active ingredient | 19.53 | 20.87 | 10.93 | 10.00 |
| Fatty/oily/waxy substance: | | | | |
| Isopropyl palmitate | 0.51 | | | 0.07 |
| Macrogol glycerol ricinoleate | 0.11 | | 0.82 | |
| Tocopheryl acetate | | 3.91 | | |
| % by wt., based on active ingred. | 3.17 | 18.74 | 7.50 | 0.70 |
| Emulsifiers: Sorbitan monolaurate | | | | 0.02 |

TABLE 2-continued

| Example No. | 6 Plantago | 7 Plantago | 8 Fol.Urticae | 9 Rad.Urticae |
|---|---|---|---|---|
| Soya lecithin + mono- and diglycerides (Metarin ®) | | | 0.11 | |
| Filler: Mannitol | | | 10.00 | |
| Aerosil | | 0.20 | | |
| Admixture | | | | |
| Fatty/oily/waxy phase | | | | |
| Macrogol glycerol ricinoleate | 0.01 | | | 0.01 |
| Carrier: Mannitol | 1.46 | | | 1.47 |
| % by wt., based on active ingred. | 0.05 | | | 0.10 |
| Emulsifier phase | | | | |
| Magnesium stearate | 0.08 | 0.06 | | 0.06 |
| Docusate sodium | | 0.06 | 0.06 | |
| Carrier: Mannitol | | 3.07 | 2.67 | |
| Emulsifier: % by wt., based on active ingred. | 0.41 | 0.57 | 0.55 | 0.60 |
| Antifoam phase Simethicone | 0.01 | 0.01 | 0.14 | 0.01 |
| Carrier: Mannitol | 1.46 | 3.13 | 13.52 | 1.47 |
| % by wt., based on active ingred. | 0.05 | 0.05 | 1.28 | 0.10 |
| Sum | 100 | 100 | 100 | 100 |
| Total (% by wt., based on active ingred.) | | | | |
| Fatty/oily/waxy substance: | 3.22 | 18.74 | 7.50 | 0.80 |
| Emulsifier: | 0.41 | 0.57 | 1.56 | 0.80 |
| Antifoam: | 0.05 | 0.05 | 1.28 | 0.10 |
| | 100 | 100 | 100 | 100 |
| Tablet weight [mg] | 3410 | 3110 | 3660 | 3400 |
| Dissolution time [sec] | 110 | 120 | 100 | 100 |

TABLE 3

| Example No. | 10 Solidago | 11 Solidago | 12 Solidago | 13 Solidago |
|---|---|---|---|---|
| Effervescent base | 71.38 | 71.38 | 71.37 | 70.00 |
| Active ingredient phase | | | | |
| Active ingredient | 13.05 | 13.05 | 13.05 | 12.80 |
| Fatty/oily/waxy substance: | | | | |
| Triglyceride of caprylic and capric acid (Miglyol ®) | 0.53 | 0.53 | 0.53 | 1.15 |
| Hydrogenated coconut oil | | | 0.18 | 0.29 |
| Triglyceride of myristic acid (Dynasan ®) | | 0.18 | | |
| Hydrogenated castor oil (Cutina ®) | 0.18 | | | |
| % by wt., based on active ingredient | 5.44 | 5.44 | 5.44 | 11.25 |
| Emulsifiers | | | | |
| Polyoxyethylene glycerol fatty acid ester (Tagat ®) | 0.18 | | 0.18 | 0.29 |
| Soya lecithin | | 0.18 | | |
| Polyoxyethylene (20) sorbitan monolaurate (Tween ®) | | | 0.01 | |
| % by wt., based on active ingredient | 1.38 | 1.38 | 1.46 | 2.27 |
| Antifoam: Simethicone | | | | 0.17 |
| % by wt., based on active ingredient | | | | 1.33 |
| Filler: Lactose | 11.75 | 11.75 | 11.75 | 5.76 |
| Admixture | | | | |
| Fillers Sorbitol | | | | 6.66 |
| Sodium sulphate | 2.94 | 2.94 | 2.94 | 2.88 |
| Sum | 100 | 100 | 100 | 100 |
| Total (% by wt., based on active ingred.) | | | | |
| Fatty/oily/waxy substance: | 5.44 | 5.44 | 5.44 | 11.25 |
| Emulsifier: | 1.38 | 1.38 | 1.46 | 2.27 |
| Antifoam: | | | | 1.33 |
| Tablet weight [mg] | 3503 | 3503 | 3503 | 3340 |
| Dissolution time [sec] | 210 | 210 | 220 | 165 |

TABLE 4

| Example No. | 14 Solidago | 15 Solidago | 16 Solidago | 17 Solidago |
|---|---|---|---|---|
| Effervescent base | 70.20 | 56.36 | 82.18 | 53.67 |
| Active ingredient phase | | | | |
| Active ingredient | 12.83 | 10.30 | 12.58 | 12.80 |
| Fatty/oily/waxy substance: | | | | |
| Isopropyl palmitate | | | 0.69 | |
| Triglyceride of caprylic and capric acid (Miglyol ®) | | 0.70 | | 0.87 |
| Unhydrogenated coconut oil | 0.29 | | | |
| % by wt., based on active ingredient | 2.26 | 6.80 | 5.48 | 6.80 |
| Emulsifier: Sorbitan monostearate | | | 0.07 | |
| Sorbitan monoisostearate | | 0.05 | | |
| Sodium stearoyllactate | | | 0.01 | |
| Polyoxyethylene glycerol fatty acid ester/Tagat ® | 0.29 | | | 0.87 |
| % by wt., based on active ingredient | 2.26 | 0.49 | 0.64 | 6.80 |
| Antifoam: Simethicone | 0.17 | 0.19 | 0.14 | |
| % by wt., based on active ingredient | 1.33 | 1.84 | 1.11 | |
| Filler: Lactose | 5.78 | 4.64 | | 8.67 |
| Sorbitol | | 0.23 | | |
| Admixture | | | | |
| Fatty/oily/waxy phase | | | | |
| Macrogol glycerol ricinoleate | | | 0.04 | |
| Carrier: Mannitol | | | 4.21 | |
| % by wt., based on active ingredient | | | 0.34 | |
| Emulsifier: Magnesium stearate | | | 0.09 | |
| % by wt., based on active ingredient | | | 0.72 | |
| Antifoam phase Simethicone | | 0.12 | | 0.12 |
| Carrier: Mannitol | | 11.48 | | 14.33 |
| Antifoam: | | | | |
| % by wt., based on active ingredient | | 1.17 | | 0.94 |
| Fillers Mannitol | | 8.12 | | |
| Sorbitol | 7.54 | | | 5.78 |
| Lactose | | 7.82 | | |
| Sodium sulphate | 2.89 | | | |
| Sum | 100 | 100 | 100 | 100 |
| Total (% by wt., based on active ingred.) | | | | |
| Fatty/oily/waxy substance: | 2.26 | 6.80 | 5.82 | 6.80 |
| Emulsifier | 2.26 | 0.49 | 1.36 | 6.80 |
| Antifoam: | 1.33 | 3.01 | 1.11 | 0.94 |
| Tablet weight [mg] | 3460 | 4310 | 3533 | 3504 |
| Dissolution time [sec] | 230 | 115 | 145 | 150 |

Solidago and birch leaf extracts both have high saponin content but nevertheless require a different fat and emulsifier phase. While preferably Carbowax 400 is used as a fatty substance and Metarin (a phospholipid) is used as an emulsifier in the case of the birch leaves, Miglyol as the fatty substance and sorbitan monoisostearate as the emulsifier have given the best results in the case of the solidago extract. In these examples, the dissolution properties are also relevant in addition to the foam formation, i.e. foam control is of primary interest in the case of the birch leaf extract since the birch leaf extracts have not increased the dissolution time to such a great extent as is the case for solidago. In the case of the solidago extract, apart from foam control the reduction of the dissolution time from almost 20 minutes to less than 4 minutes is of primary interest and could be achieved by the measure described. Owing to the many ingredients in each case, almost every extract exhibits its very own behavior so that it is necessary in each case to establish the optimum on the basis of the available information.

Effervescent tablets which are not treated or prepared according to the invention initially begin to effervesce at the surface in water; however, the effervescent effect and hence the dissolution are increasingly slowed down by the formation of a highly concentrated, tacky, slimy solution between the effervescent granules. Consequently, the further admission of water into the core of the effervescent tablet is prevented, so that said core remains dry and the dissolution takes place correspondingly slowly.

What is claimed is:

1. An effervescent formulation in the form of granules or of a tablet, containing at least one water-soluble or at least suspendable dry plant extract and an effervescent base comprising at least one solid, edible, organic acid and at least one alkali metal and/or alkaline earth metal carbonate or bicarbonate, wherein the dry plant extract particles are coated with at least one oily, fatty or waxy substance.

2. The effervescent formulation as claimed in claim 1, wherein the plant extract originates from at least one of the plants or plant parts selected from the group consisting of ivy, sabale, solidago, plantago, nettle root, nettle leaves, birch leaves, cynara, thyme, hypericum, harpagophytum, gingko and Ruscus aculeatus.

3. The effervescent formulation as claimed in claim 1, wherein the oily, fatty or waxy substance comprises at least one substance selected from the group consisting of neutral oils, glycerol, polypropylene glycol esters of caprylic acid and capric acid, edible animal or vegetable fats, microcrystalline triglycerides and glyceryl esters of saturated, even-numbered and unbranched higher fatty acids in the order of magnitude $C_{10}$ to $C_{22}$, hydrogenated coconut oil, tocopheryl acetate, esters of higher fatty acids, isopropyl palmitate, and polyethylene glycols.

4. The effervescent formulation as claimed in claim 1, which additionally contains 0.05 to 0.5 parts by weight—per 100 parts by weight of plant extract—of the oily, fatty or waxy substance, in mixture with the other components.

5. The effervescent formulation as claimed in claim 1, which furthermore contains at least one emulsifier, selected from the group consisting of phospholipids, polysorbates, ethoxylated glycerol fatty acid esters, sugar esters, glycerol polyethylene glycol oxystearate, Macrogol glycerol ricinoleate, sodium stearoyllactate and lipid emulsifiers, propylene glycol stearate, and glyceryl oleate, laurate and stearate.

6. The effervescent formulation as claimed in claim 5, wherein at least part of the emulsifier is present in an amount of 0.3–3.0 parts by weight per 100 parts by weight of plant extract in the coating and/or on a carrier in mixture with the other components.

7. The effervescent formulation as claimed in claim 1, which furthermore contains an antifoam.

8. The effervescent formulation as claimed in claim 7, wherein at least a part of the antifoam is contained in the coating and/or on a carrier in mixture with the other components.

9. The effervescent formulation as claimed in claim 1, which furthermore contains at least one additive and/or excipient selected from the group consisting of pharmaceutically permissible fillers, emulsifiers, hydrocolloids, flavors, artificial sweeteners and surfactants.

10. A process for the preparation of an effervescent formulation in the form of granules or of a tablet, containing at least one water-soluble or at least suspendable dry plant extract and an effervescent base comprising at least one solid, edible, organic acid and at least one alkali metal and/or alkaline earth metal carbonate or bicarbonate, wherein the dry plant extract particles are heated and wet with or mixed with a melt or solution of the oily, fatty or waxy substance, sieved to the desired particle size and mixed with said effervescent base.

11. The process as claimed in claim 10, wherein at least one substance selected from the group consisting of pharmaceutically permissible fillers, hydrocolloids, flavors, artificial sweeteners, emulsifiers and antifoams is added to the melt or solution.

12. The process as claimed in claim 11, at least comprising one filler, wherein said filler is heated and is wet or mixed with at least one substance selected from the group consisting of a melt or solution of the oily, fatty or waxy substance and at least one antifoam, and is then dried and sieved to the desired particle size.

13. The effervescent formulation as claimed in claim 3, wherein the oily, fatty or waxy substance is present in an amount of 0.5 to 25 parts by weight 100 parts by weight of plant extract.

14. The effervescent formulation as claimed in claim 13, wherein the oily, fatty or waxy substance is present in an amount of 0.8 to 19 parts by weight per 100 parts by weight of plant extract.

15. The effervescent formulation as claimed in claim 4, wherein the additional oily, fatty or waxy substance is present on a carrier.

16. The effervescent formulation as claimed in claim 4, wherein the additional oily, fatty or waxy substance is present in an amount of 0.1 to 0.4 parts by weight per 100 parts by weight of plant extract.

17. The effervescent formulation as claimed in claim 5, wherein said at least one emulsifier is present in an amount of 0.2 to 10 parts by weight per 100 parts by weight of plant extract.

18. The effervescent formulation as claimed in claim 6, wherein said at least part of the emulsifier is present in an amount of 0.4 to 1.5 parts by weight per 100 parts by weight of plant extract.

19. The effervescent formulation as claimed in claim 7, wherein the antifoam is present in 0.05 to 10 parts by weight per 100 parts by weight of plant extract.

20. The effervescent formulation as claimed in claim 17, wherein the antifoam is present in 0.6 to 3.0 parts by weight 100 parts by weight of plant extract.

21. The effervescent formulation as claimed in claim 7, wherein the antifoam is dimethicone or simethicone.

22. The effervescent formulation as claimed in claim 8, wherein said at least part of the antifoam is present in an amount of about 0.06 to 1.5 parts by weight per 100 parts by weight of plant extract.

23. The process as claimed in claim 10, wherein at least one of wetting, mixing and drying is carried out in vacuo.

* * * * *